US012491108B2

(12) United States Patent
Jo et al.

(10) Patent No.: US 12,491,108 B2
(45) Date of Patent: Dec. 9, 2025

(54) CONTRACEPTION APPARATUS FOR MALE

(71) Applicant: IUCF-HYU (INDUSTRY-UNIVERSITY COOPERATION FOUNDATION HANYANG UNIVERSITY), Seoul (KR)

(72) Inventors: Jung Ki Jo, Seoul (KR); Hongyun So, Seoul (KR)

(73) Assignee: IUCF-HYU (INDUSTRY-UNIVERSITY COOPERATION FOUNDATION HANYANG UNIVERSITY), Seoul (KR)

( * ) Notice: Subject to any disclaimer, the term of this patent is extended or adjusted under 35 U.S.C. 154(b) by 294 days.

(21) Appl. No.: 18/035,387

(22) PCT Filed: Sep. 16, 2021

(86) PCT No.: PCT/KR2021/012658
§ 371 (c)(1),
(2) Date: Jun. 30, 2023

(87) PCT Pub. No.: WO2022/097908
PCT Pub. Date: May 12, 2022

(65) Prior Publication Data

US 2023/0414403 A1 Dec. 28, 2023

(30) Foreign Application Priority Data

Nov. 4, 2020 (KR) ........................ 10-2020-0145944

(51) Int. Cl.
*A61F 6/22* (2006.01)
*A61F 6/20* (2006.01)

(52) U.S. Cl.
CPC ................ *A61F 6/22* (2013.01); *A61F 6/202* (2013.01)

(58) Field of Classification Search
CPC .. A61F 2/01; A61F 2/0022; A61F 2/02; A61F 2/22; A61F 6/22; A61F 6/202;
(Continued)

(56) References Cited

U.S. PATENT DOCUMENTS

2018/0185096 A1 7/2018 Eisenfrats et al.
2019/0060530 A1 2/2019 Choudhury et al.

FOREIGN PATENT DOCUMENTS

CN 2529622 Y 1/2003
CN 201595993 U 10/2010
(Continued)

OTHER PUBLICATIONS

Korean Notice of Allowance for KR 10-2020-0145944 dated Aug. 2, 2022.
(Continued)

*Primary Examiner* — Ophelia A Hawthorne
(74) *Attorney, Agent, or Firm* — Sughrue Mion, PLLC

(57) ABSTRACT

A male contraception apparatus includes a tube configured for insertion into the seminal duct. The tube has a hollow portion open at both ends. Positioned within the hollow portion is at least one filter. The filter includes a plurality of microchannels that extend through the filter and a plurality of nanospikes formed on one surface.

10 Claims, 8 Drawing Sheets

(58) Field of Classification Search
CPC .. A61F 2/00; A61F 2/0077; A61F 2002/0081; A61F 2002/009; A61F 6/225; A61F 6/02; A61F 6/20; A61B 17/1204; A61B 17/12172; A61B 17/12177
See application file for complete search history.

(56) References Cited

FOREIGN PATENT DOCUMENTS

| | | | | |
|---|---|---|---|---|
| JP | 2006-198404 | A | | 8/2006 |
| JP | 2018-515313 | A | | 6/2018 |
| KR | 10-1999-0007958 | A | | 1/1999 |
| KR | 20180153735 | A | * | 12/2018 |
| KR | 10-2020-0066960 | A | | 6/2020 |
| WO | 2006/081238 | A2 | | 8/2006 |
| WO | 2016/180426 | A1 | | 11/2016 |

OTHER PUBLICATIONS

International Search Report for PCT/KR2021/012658 dated Jan. 7, 2022.
Office Action issued May 7, 2024 in Japanese Application No. 2023-527360.
Notice of Allowance dated Aug. 27, 2024, which issued during the prosecution of Japanese Patent Application No. 2023-527360.

* cited by examiner

[FIG. 1]
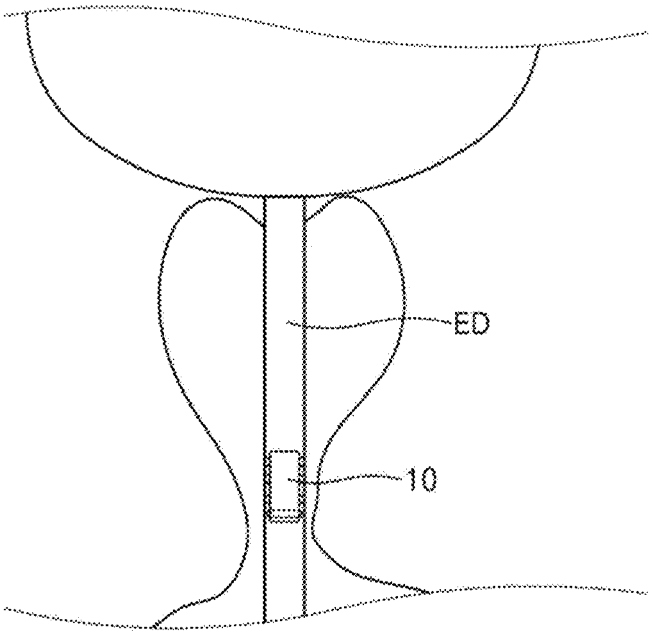
[FIG. 2]
10
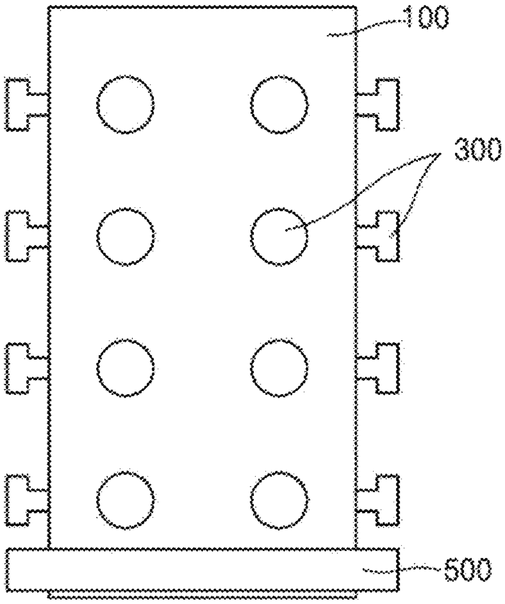

[FIG. 3]
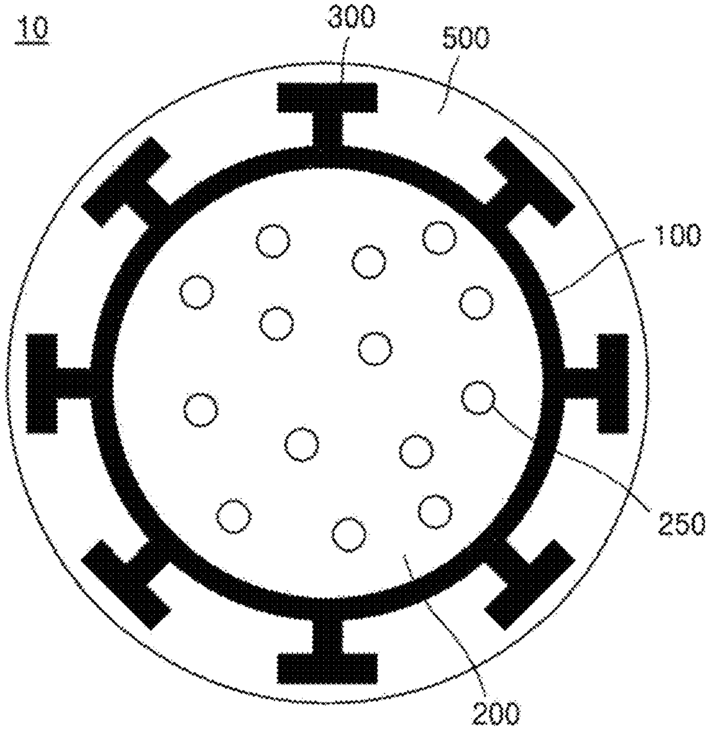

[FIG. 4]
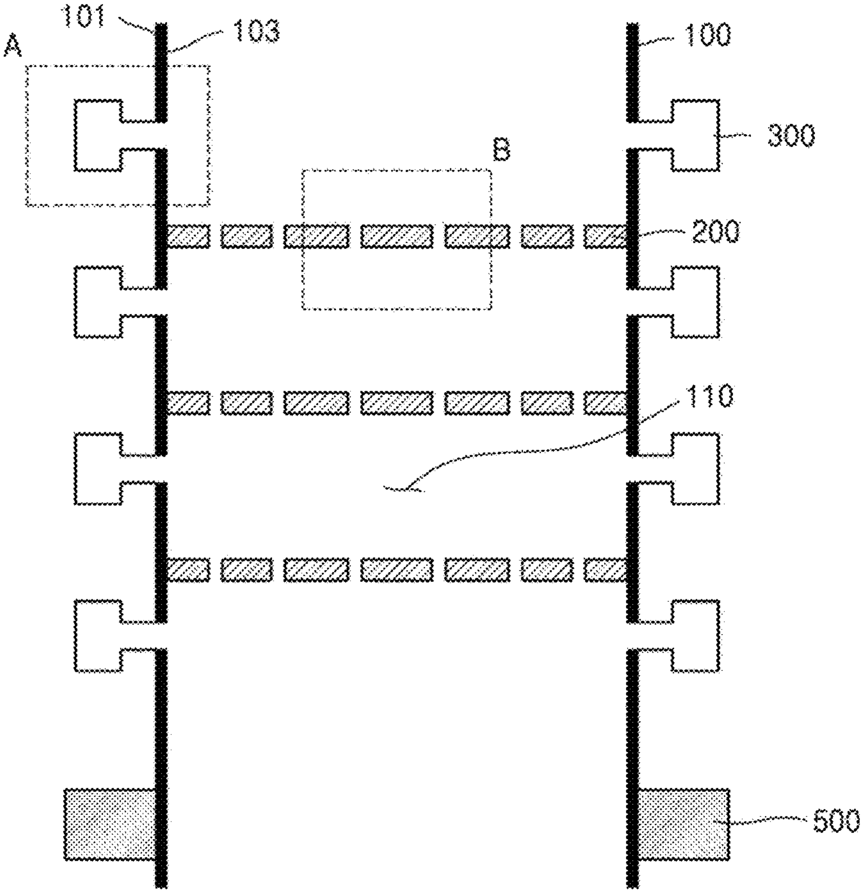

[FIG. 5]
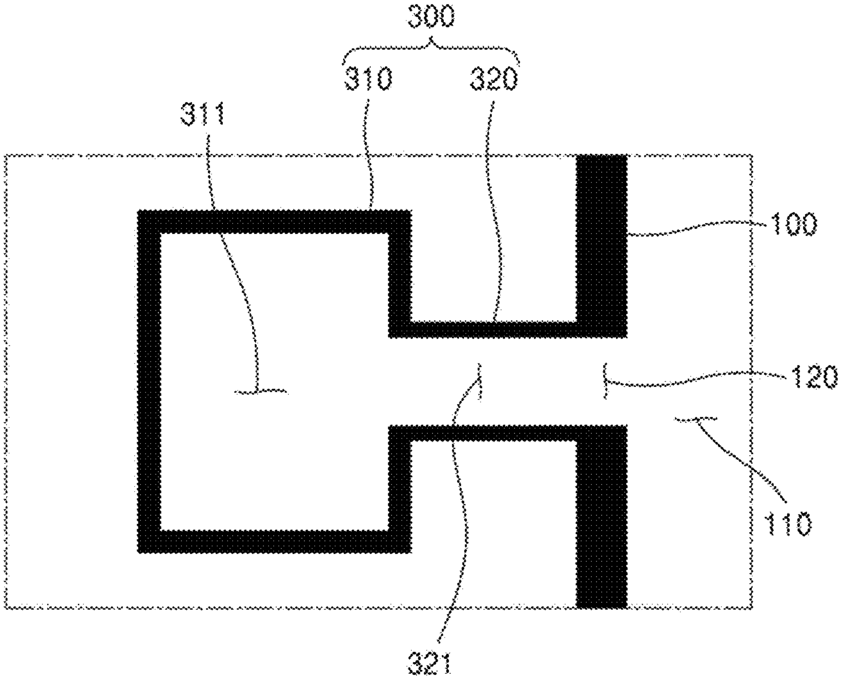
[FIG. 6]
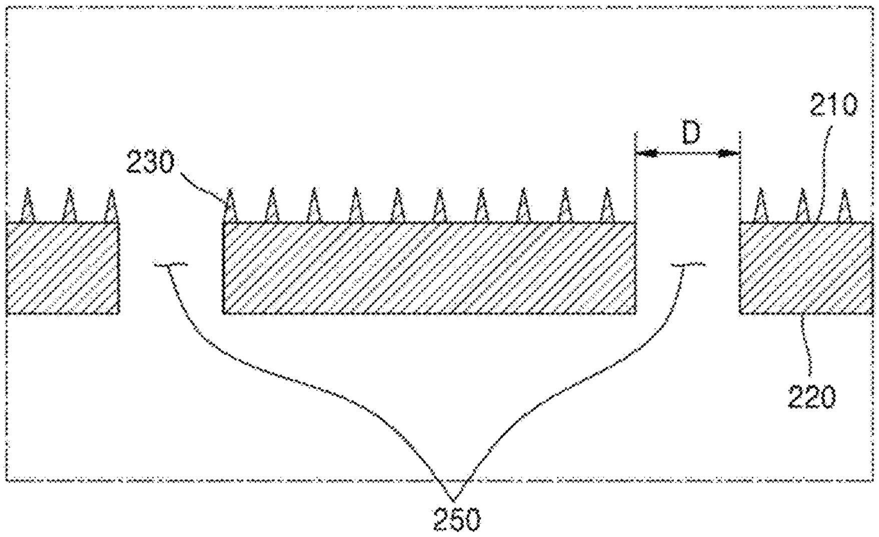

[FIG. 7]
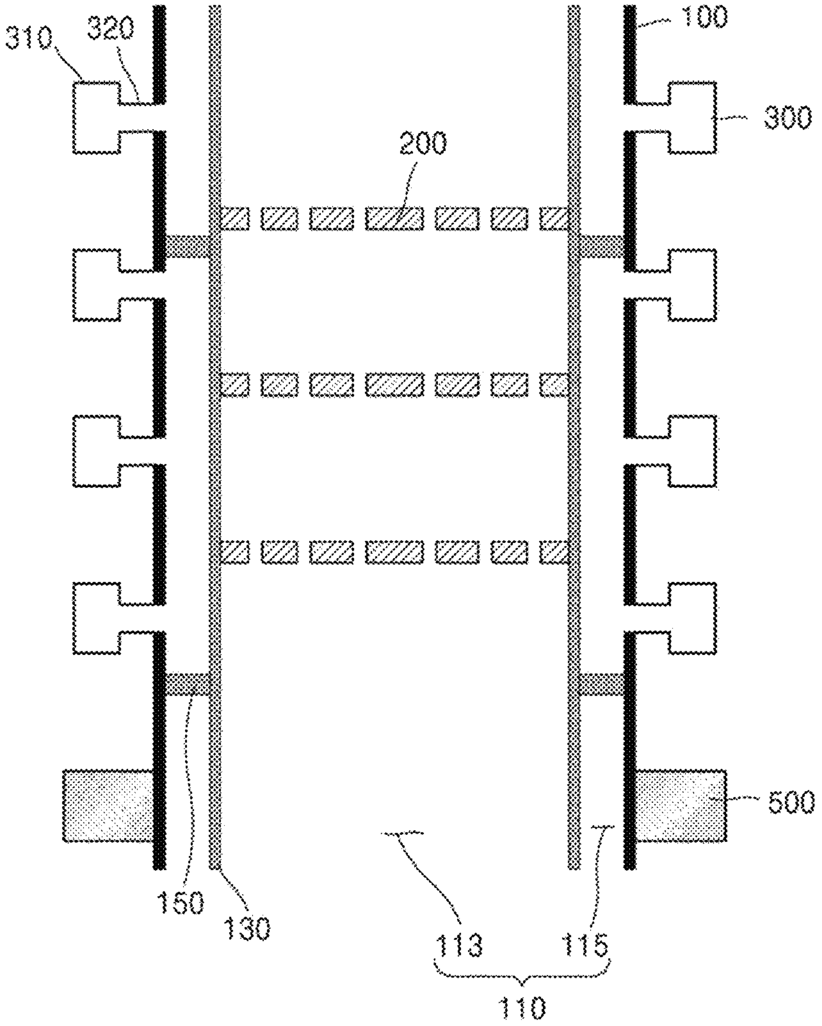

[FIG. 8]
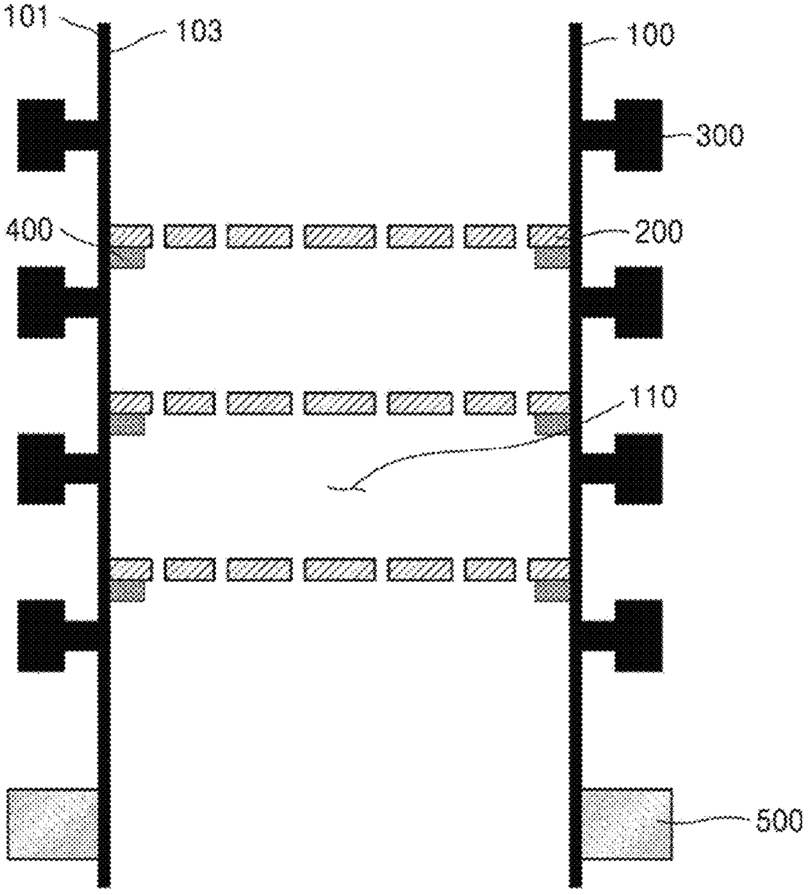

[FIG. 9]
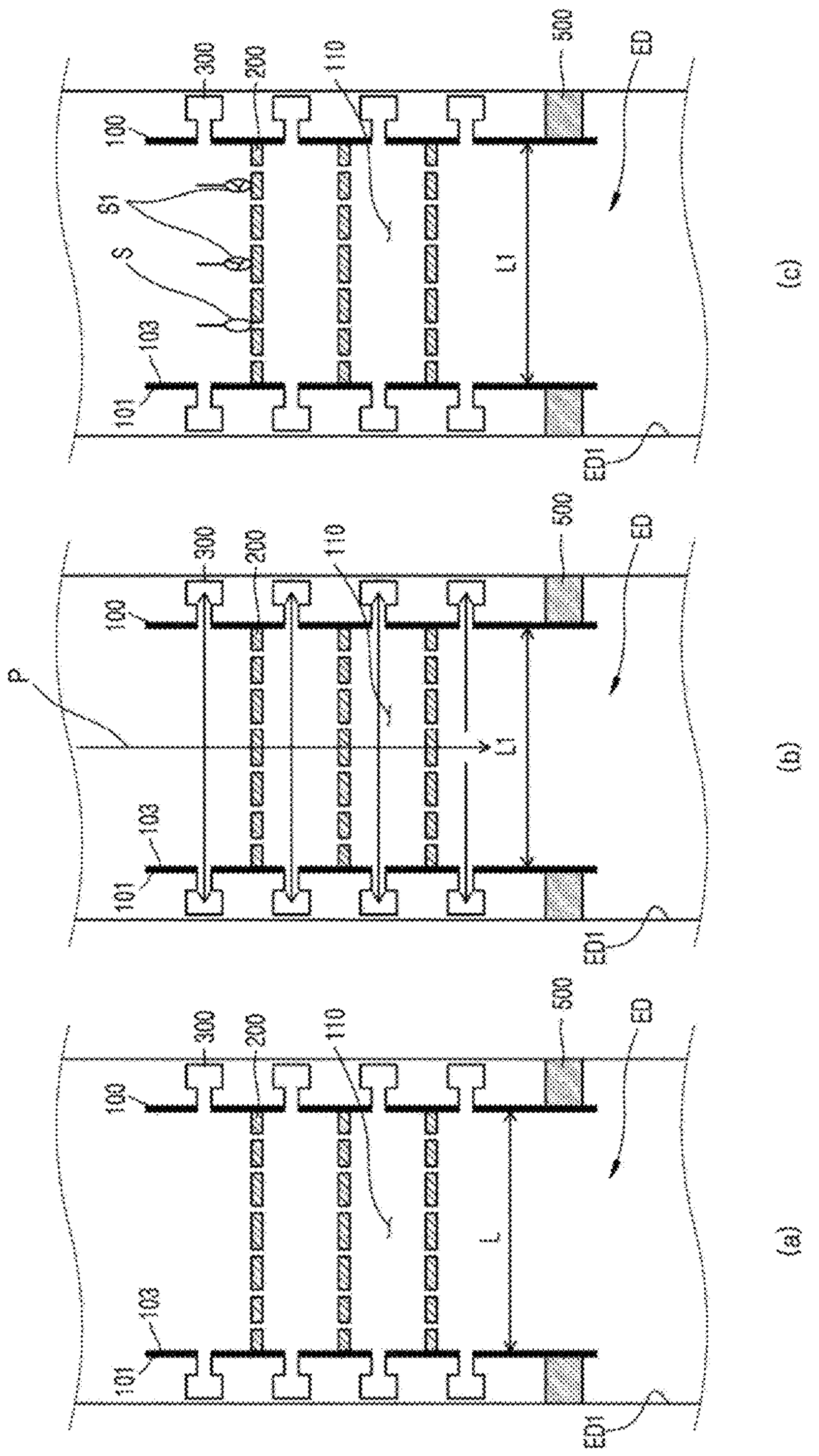

[FIG. 10]
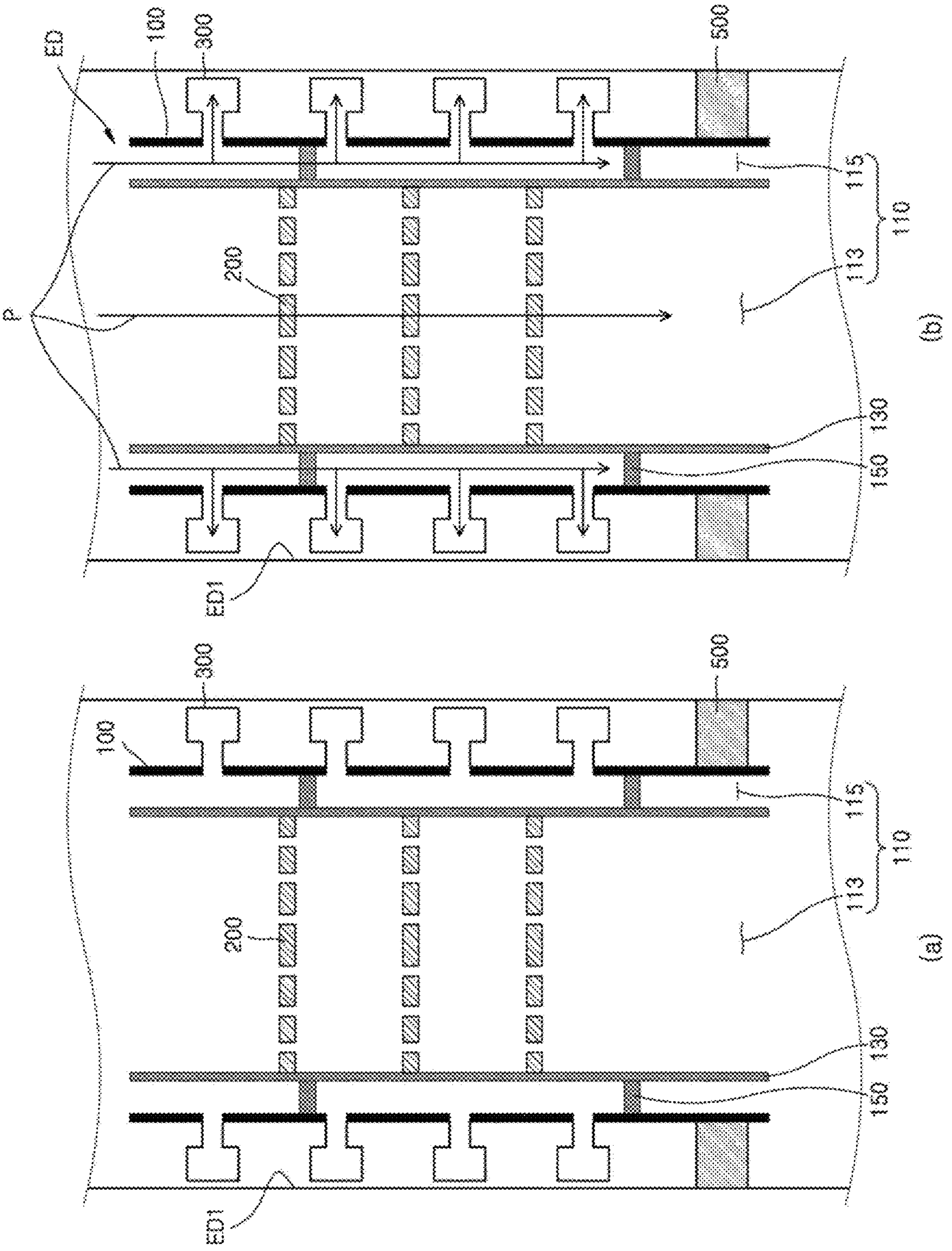

CONTRACEPTION APPARATUS FOR MALE

TECHNICAL FIELD

The present invention relates to a male contraceptive device, and more specifically to a reversible male contraceptive device that is easy to insert into and remove from the ejaculatory duct and can be used semi-permanently.

BACKGROUND ART

Condoms are usually used as male disposable contraceptives. Condoms are worn on the penis prior to sexual intercourse and are disposed of after use. The use of condoms is required every time sexual intercourse is attempted, causing inconvenience to users.

Due to this inconvenience, a vasectomy can be performed as a surgical procedure for male contraception. A vasectomy is an operation in which the vas deferens is cut and the two cut ends of the vas deferens are stitched to block sperm from travelling through the vas deferens. It can be said to be more effective than other contraceptive methods and has the advantage of being permanent. When it intends to eliminate the contraceptive effect of vasectomy as required, a vasectomy reversal is performed to reconnect the vas deferens after the previous vasectomy. However, the vasectomy reversal has a probability of failure.

Under these circumstances, studies are currently underway on male contraceptive devices that are easy to insert into and remove from the human body while maintaining their contraceptive effects.

DETAILED DESCRIPTION OF THE INVENTION

Problems to be Solved by the Invention

The present invention has been made in an effort to solve the problems of the prior art and intends to provide a male contraceptive device that is easy to insert into and remove from the ejaculatory duct while minimizing side effects and sequelae.

The present invention also intends to provide a reversible male contraceptive device that can be used semi-permanently with good contraceptive efficacy.

Objects of the present invention are not limited to the above-mentioned objects and other unmentioned objects may be clearly understood by those skilled in the art from the following description.

Means for Solving the Problems

A male contraceptive device according to an embodiment of the present invention includes: a tube having an internal hollow whose both ends are open and insertable into the ejaculatory duct; and at least one filter located in the hollow of the tube, wherein the filter includes a plurality of microchannels passing therethrough and a plurality of nanospikes formed on one surface thereof.

In one embodiment, the male contraceptive device may include a plurality of pressing members arranged on an outer surface of the tube and spaced apart from each other.

In one embodiment, the tube may further include a plurality of through-holes penetrating an inner surface thereof in contact with the hollow and the outer surface thereof and each of the pressing members may include a pressing portion having an accommodation space therein and a connection portion connecting the pressing portion and the tube and having a connection hole through which the corresponding through-hole is in communication with the accommodation space.

In one embodiment, the tube may further include a partition wall located in the hollow to partition the hollow into an inner space and an outer space and a plurality of through-holes penetrating the inner surface in contact with the outer space and the outer surface, and the outer space may be located outside the inner space to surround the inner space.

In one embodiment, each of the pressing members may include a pressing portion having an accommodation space therein and a connection portion connecting the pressing portion and the tube and having a connection hole through which the corresponding through-hole is in communication with the accommodation space.

In one embodiment, the pressing members may be arranged at regular intervals along the circumference of the tube.

In one embodiment, the male contraceptive device may further include a movement-preventing member located at one side of the tube and surrounding the tube wherein the movement-preventing member is made of a material that expands at a preset temperature.

In one embodiment, the tube may be made of a stretchable material.

In one embodiment, the filter may be provided in plurality and the plurality of filters may be arranged along the lengthwise direction of the tube.

In one embodiment, the tube may further include a flange member protruding from the inner surface to support the other surface of the filter.

Prior to the detailed description of the invention, it should be understood that the terms and words used in the specification and the claims are not to be construed as having common and dictionary meanings but are construed as having meanings and concepts corresponding to the technical spirit of the present invention in view of the principle that the inventor can define properly the concept of the terms and words in order to describe his/her invention with the best method.

Effects of the Invention

The male contraceptive device of the present invention is easy to insert into and remove from the ejaculatory duct, causing minimal side effects and sequelae. In addition, the male contraceptive device of the present invention can physically destroy sperm, achieving improved contraceptive efficacy. Furthermore, the male contraceptive device of the present invention can be used semi-permanently.

Effects of the present invention are not limited to the above-mentioned effects and other unmentioned effects may be clearly understood by those skilled in the art from the description of the claims.

BRIEF DESCRIPTION OF THE DRAWINGS

FIG. 1 is a schematic view illustrating a state in which a male contraceptive device according to one embodiment of the present invention is inserted into the ejaculatory duct.

FIG. 2 is a schematic view illustrating the male contraceptive device of FIG. 1.

FIG. 3 is a plan view illustrating the male contraceptive device of FIG. 2.

FIG. 4 is a cross-sectional view illustrating the male contraceptive device of FIG. 2.

FIG. 5 is an enlarged view illustrating a portion "A" of FIG. 4.

FIG. 6 is an enlarged view illustrating a portion "B" of FIG. 4.

FIG. 7 is a schematic view illustrating a male contraceptive device according to a further embodiment of the present invention.

FIG. 8 is a schematic view illustrating a male contraceptive device according to another embodiment of the present invention.

FIG. 9 schematically illustrates a procedure in which the male contraceptive device of FIG. 2 is brought into close contact with the inner wall of the ejaculatory duct.

FIG. 10 schematically illustrates a procedure in which the male contraceptive device of FIG. 7 is brought into close contact with the inner wall of the ejaculatory duct.

BEST MODE FOR CARRYING OUT THE INVENTION

Other objects, advantages, and novel features of the invention will become more apparent from the following detailed description and preferred embodiments with reference to the appended drawings. In the drawings, the same elements are denoted by the same reference numerals even though they are depicted in different drawings. Although such terms as "first" and "second," etc. may be used to describe various elements, these elements should not be limited by above terms. These terms are used only to distinguish one element from another. In the description of the present invention, detailed explanations of related art are omitted when it is deemed that they may unnecessarily obscure the essence of the present invention.

Preferred embodiments of the present invention will now be described in detail with reference to the accompanying drawings.

FIG. 1 is a schematic view illustrating a state in which a male contraceptive device according to one embodiment of the present invention is inserted into the ejaculatory duct.

Referring to FIG. 1, the male contraceptive device 10 can be inserted into the ejaculatory duct (ED). Particularly, the male contraceptive device 10 can be inserted into and removed from the ejaculatory duct (ED) through a urologic surgery using a cystoscope. Since the male contraceptive device 10 is surgically inserted into the ejaculatory duct (ED), it provides effective and semi-permanent contraception without causing inconvenience in daily life.

The user can remove the male contraceptive device 10 from the ejaculatory duct (ED) at any desired time without any damage to the human body. That is, the male contraceptive device 10 can be reversibly removed with minimal side effects and sequelae. Details of the male contraceptive device 10 will be described below.

FIG. 2 is a schematic view illustrating the male contraceptive device of FIG. 1, FIG. 3 is a plan view illustrating the male contraceptive device of FIG. 2, FIG. 4 is a cross-sectional view illustrating the male contraceptive device of FIG. 2, FIG. 5 is an enlarged view illustrating a portion "A" of FIG. 4, and FIG. 6 is an enlarged view illustrating a portion "B" of FIG. 4.

Referring to FIGS. 2 to 6, the male contraceptive device 10 may include a tube 100, a filter 200, and pressing members 300. The male contraceptive device 10 may further include a movement-preventing member 500.

The tube 100 may be provided in a barrel shape. In an embodiment, the tube 100 may be provided in a cylindrical shape. In an alternative embodiment, the tube may be provided in a polygonal cylindrical shape such as a rectangular or hexagonal cylindrical shape. The barrel-shaped tube 100 may have an internal hollow 110 whose both ends are open. In an embodiment, the hollow 110 may have an inlet, through which semen enters, formed at one end thereof and an outlet, through which the semen exits, formed at the other end thereof. In an embodiment, the length of the tube 100 may be about 0.5 cm to 3 cm but is not limited thereto.

The tube 100 may be inserted into the ejaculatory duct (ED). In this case, the tube 100 is smaller in width than the ejaculatory duct (ED). The tube 100 may be made of a stretchable material. In this case, the tube 100 inserted into the ejaculatory duct (ED) can be expanded by the hydraulic pressure of semen flowing in the ejaculatory duct (ED). In an embodiment, the tube 100 may be made of a polymeric material (e.g., silicone) harmless to humans but is not limited to this material.

The tube 100 may include an outer surface 101 and an inner surface 103. The inner surface 103 may surround the hollow 110 of the tube 100 while being in contact with the hollow 110. The tube 100 may include a plurality of through-holes 120 penetrating the outer surface 101 and the inner surface 103.

The through-holes 120 may be in communication with the hollow 110. The through-holes 120 may be spaced apart from each other. The through-holes 120 may be arranged along the circumference of the tube 100. In an embodiment, the through-holes 120 may be arranged at regular intervals along the circumference of the tube 100. The through-holes 120 may be arranged along the lengthwise direction of the tube 100.

As described above, the male contraceptive device 10 may include at least one filter 200. In an embodiment, the male contraceptive device 10 may include a plurality of filters 200. The filters 200 may be located in the hollow 110 of the tube 100. The filters 200 may be spaced apart from each other. The filters 200 may be arranged along the lengthwise direction of the tube 100.

Although not illustrated in the drawings, in an embodiment, the tube 100 may include a plurality of insertion grooves (not illustrated) recessed from the inner surface 103 towards the outer surface 101. Each of the filters 200 may be fixedly inserted into the corresponding insertion groove in the tube 100.

The filter 200 may destroy sperm in semen entering the tube 100 while filtering out the sperm. The filter 200 may pass seminal substances smaller than a predetermined size (e.g., substances having a size smaller than the size of sperm). In an embodiment, the filter 200 may be made of a silicone material but is not limited to this material.

The filter 200 may include one surface 210 and the other surface 220 opposite to each other. In an embodiment, the one surface 210 of the filter 200 may be formed in the direction toward the inlet of the hollow 110. The other surface 220 of the filter 200 opposite to the one surface 210 may be formed in the direction toward the outlet of the hollow 110. The filter 200 may include a plurality of microchannels 250 passing therethrough and a plurality of nanospikes 230.

The microchannels 250 may connect the one surface 210 and the other surface 220 of the filter 200. The microchannels 250 may be spaced apart from each other. In an embodiment, the microchannels 250 may be irregularly arranged as viewed from above.

In an alternative embodiment, the microchannels 250 may be regularly arranged as viewed from above. The width (D) of the microchannels 250 may be smaller than that of sperm to prevent sperm from passing through the filter 200 through the microchannels 250. In an embodiment, the width (D) of the microchannels 250 may be about 3 μm to 5 μm but is not limited thereto.

The nanospikes 230 may be formed on the one surface 210 of the filter 200. In an embodiment, the nanospikes 230 may be irregularly arranged as viewed from above but are not limited to this arrangement. In an embodiment, each of the nanospikes 230 may have a sharp end. This shape enables the nanospikes 230 to destroy sperm. The physical destruction of sperm by the nanospikes 230 leads to an improvement in contraceptive performance.

The pressing members 300 may be located on the outer surface 101 of the tube 100. The pressing members 300 may be spaced apart from each other. The pressing members 300 may be arranged at regular intervals along the circumference of the tube 100.

The pressing members 300 may be brought into close contact with the inner wall (ED1) of the ejaculatory duct (ED) to prevent the tube 100 from being moved by the pressure of entering semen. The pressing members 300 may be made of a stretchable material. For example, the pressing members 300 may be made of a silicone material. Each of the pressing members 300 may include a pressing portion 310 and a connection portion 320.

In an embodiment, the pressing portion 310 may include an accommodation space 311. The connection portion 320 may connect the pressing portion 310 and the tube 100. The connection portion 320 may include a connection hole 321 passing therethrough. The connection hole 321 may be in communication with the corresponding through-hole 120. Thus, the accommodation space 311 may be in communication with the corresponding through-hole 120 through the connection hole 321.

The movement-preventing member 500 may be located at one side of the tube 100. In an embodiment, the movement-preventing member 500 may be located adjacent to the outlet of the hollow 110 but is not limited to this location. The movement-preventing member 500 may surround the tube 100. The movement-preventing member 500 may be larger in width than the tube 100. In an embodiment, the movement-preventing member 500 may be provided in a ring shape.

The movement-preventing member 500 may be brought into contact with the inner wall (ED1) of the ejaculatory duct (ED) to limit the movement of the tube 100 after insertion into the ejaculatory duct (ED).

The movement-preventing member 500 may be made of a material that expands at a preset temperature. For example, the movement-preventing member 500 may be made of a shape memory alloy. In this case, the movement-preventing member 500 may expand at body temperature (~36.5° C.) to come into contact with the inner wall (ED1) of the ejaculatory duct (ED).

FIG. 7 is a schematic view illustrating a male contraceptive device according to a further embodiment of the present invention. Most of the components illustrated in FIG. 7 are the same as those illustrated in FIGS. 1 to 6 and descriptions thereof are omitted or only briefly mentioned for convenience of explanation.

Referring to FIG. 7, the male contraceptive device 10 may include a tube 100, a filter 200, pressing members 300, and a movement-preventing member 500.

The tube 100 may include a hollow 110, through-holes 120, a partition wall 130, and a support portion 150. The partition wall 130 may be located in the hollow 110. The partition wall 130 may partition the hollow 110 into an inner space 113 and an outer space 115. Accordingly, the inner space 113 and the outer space 115 may not be connected to each other.

The inner space 113 may be located within the partition wall 130. The inner space 113 may be in the form of a hollow whose both ends are open because it is located in the hollow 110 and forms a portion of the hollow 110.

The outer space 115 may be located outside the partition wall 130. That is, the outer space 115 may be located between the partition wall 130 and the inner surface 103 of the tube 100. The outer space 115 may surround the inner space 113.

The support portion 150 may be located between and connect the partition wall 130 and the inner surface 103 of the tube 100. The support portion 150 may be made of a stretchable material. Although the expansion of the tube 100 leads to an increase in distance between the inner surface 103 of the tube 100 and the partition wall 130, the support portion 150 can connect the partition wall 130 and the inner surface 103.

The filter 200 may be provided in plurality. The filters 200 may be located in the hollow 110. In an embodiment, the filters 200 may be located in the inner space 113. The boundary of the filter 200 may be in contact with the partition wall 130. The filter 200 may include a plurality of microchannels 250 and a plurality of nanospikes 230.

Each of the pressing members 300 may include a connection portion 320 and a pressing portion 310. The pressing portion 310 may include an accommodation space 311. The connection portion 320 may include a connection hole 321.

FIG. 8 is a schematic view illustrating a male contraceptive device according to another embodiment of the present invention. Most of the components illustrated in FIG. 8 are the same as those illustrated in FIGS. 1 to 6 and descriptions thereof are omitted or only briefly mentioned for convenience of explanation.

Referring to FIG. 8, the male contraceptive device 10 may include a tube 100, a filter 200, pressing members 300, and a movement-preventing member 500.

The tube 100 may include an outer surface 101, an inner surface 103, a hollow 110, and a flange member 400. The flange member 400 may protrude from the inner surface 103 of the tube 100. In an embodiment, the flange member 400 may be disposed along the circumference of the tube 100. The flange member 400 may support the other surface 220 of the filter 200 located in the hollow 110 to prevent the filter 200 from being moved by the pressure of entering semen or the like.

Each of the pressing members 300 may include a connection portion 320 and a pressing portion 310. In an embodiment, the formation of through-holes 120 in the tube 100 may be omitted, unlike in FIG. 4. The formation of accommodation spaces 311 and connection holes 321 in the pressing portion 310 and the connection portion 320, respectively, may be omitted, unlike in FIG. 4.

MODE FOR CARRYING OUT THE INVENTION

An operational procedure of a male contraceptive device 10 according to an embodiment of the present invention will be described.

FIG. 9 schematically illustrates a procedure in which the male contraceptive device of FIG. 2 is brought into close contact with the inner wall of the ejaculatory duct. In FIG. 9, (a) illustrates a state in which the male contraceptive device is inserted into the ejaculatory duct, (b) illustrates a state in which the pressing members of the male contraceptive device are brought into close contact with the inner wall of the ejaculatory duct when a man ejaculates, and (c) illustrates a state in which sperm in semen ejaculated by a man is destroyed by the male contraceptive device. Most of the components illustrated in FIG. 9 are the same as those illustrated in FIGS. 1 to 6 and descriptions thereof are omitted or only briefly mentioned for brevity of explanation.

Referring to (a) of FIG. 9, the male contraceptive device 10 can be inserted into the ejaculatory duct (ED) through a urologic surgery using a cystoscope. In an embodiment, the tube 100 of the male contraceptive device 10 may be smaller in width (L) than the ejaculatory duct (ED) for easy insertion of the male contraceptive device 10 into the ejaculatory duct (ED).

When the male contraceptive device 10 is inserted into the ejaculatory duct (ED), the movement-preventing member 500 of the male contraceptive device 10 may be brought into contact with the inner wall (ED1) of the ejaculatory duct (ED).

The movement-preventing member 500 may be made of a material that expands at a preset temperature. As the movement-preventing member 500 expands at the internal temperature of the ejaculatory duct (ED), it comes into close contact with the inner wall (ED1) of the ejaculatory duct (ED). This significantly restricts the movement of the male contraceptive device 10 within the ejaculatory duct (ED).

Referring to (b) of FIG. 9, when a man ejaculates, semen enters the urethra through the ejaculatory duct (ED), flows through the urethra, and exits the human body. When a man ejaculates, the internal pressure (P) of the ejaculatory duct (ED) may increase. The increased internal pressure (P) of the ejaculatory duct leads to an increase in the internal pressure (P) of the hollow 110 of the tube 100, with the result that the tube 100 expands and its width (L1) increases.

The internal pressure (P) of the hollow 110 of the tube 100 may be transmitted to the pressing members 300 through the through-holes 120. As a result, the internal pressure of the accommodation spaces 311 may also increase, resulting in expansion of the pressing members 300. As the tube 100 and the pressing members 300 expand, the pressing members 300 may be brought into close contact with the inner wall (ED1) of the ejaculatory duct (ED).

Although the close contact of the pressing members with the inner wall (ED1) of the ejaculatory duct (ED) increases the internal pressure of the ejaculatory duct (ED), the pressing members can prevent the male contraceptive device from moving in the ejaculatory duct (ED).

Referring to (c) of FIG. 9, sperm (S) in semen flows in the ejaculatory duct (ED). The semen may enter the hollow 110 of the tube 100. The sperm (S) in the semen cannot pass through the microchannels 250 of the filter 200 because its width (D) is larger than the width (D) of the microchannels 250. However, other fine substances in the semen can pass through the microchannels 250.

The sperm (S) having entered the hollow 110 of the tube 100 may collide with the nanospikes 230 of the filter 200. The sperm (S1) may be destroyed by the nanospikes 230 having sharp ends when colliding with the nanospikes 230.

The destroyed sperm (S1) is degraded into smaller sizes sufficient to pass through the microchannels 250. That is, the destroyed sperm (S1) together with the semen may exit through the male contraceptive device 10. Therefore, the male contraceptive device 10 has a contraceptive effect due to its ability to destroy sperm in semen.

FIG. 10 schematically illustrates a procedure in which the male contraceptive device of FIG. 7 is brought into close contact with the inner wall of the ejaculatory duct.

In FIG. 10, (a) illustrates a state in which the male contraceptive device is inserted into the ejaculatory duct and (b) illustrates a state in which the pressing members of the male contraceptive device are brought into close contact with the inner wall of the ejaculatory duct when a man ejaculates. Most of the components illustrated in FIG. 10 are the same as those illustrated in FIGS. 1 to 6 and descriptions thereof are omitted or only briefly mentioned for brevity of explanation.

Referring to (a) of FIG. 10, the male contraceptive device 10 can be inserted into the ejaculatory duct (ED) through a urologic surgery using a cystoscope. When the male contraceptive device 10 is inserted into the ejaculatory duct (ED), the movement-preventing member 500 of the male contraceptive device 10 may be brought into contact with the inner wall (ED1) of the ejaculatory duct (ED).

Referring to (b) of FIG. 10, when a man ejaculates, semen enters the urethra through the ejaculatory duct (ED), flows through the urethra, and exits the human body. When a man ejaculates, the internal pressure (P) of the ejaculatory duct (ED) may increase. The increased internal pressure (P) of the ejaculatory duct leads to an increase in the internal pressure (P) of the hollow 110 of the tube 100.

The increased internal pressure of the hollow 110 leads to increases in the pressure (P) of the inner space 113 and the outer space 115 of the hollow 110 partitioned by the partition wall 130. In an embodiment, the width of the partition wall 130 may be maintained constant despite an increase in the internal pressure of the hollow 110. Thus, the filters 200 located in the inner space 113 can be prevented from being separated from the partition wall 130 by a change in the pressure of the hollow 110.

The increased internal pressure (P) of the hollow 110 leads to expansion of the tube 100, resulting in an increase in the width of the tube 100. The internal pressure of the outer space 115 of the tube 100 may be transmitted to the pressing members 300 through the through-holes 120. As a result, the internal pressure of the accommodation spaces 311 may also increase, resulting in expansion of the pressing members 300. As the tube 100 and the pressing members 300 expand, the pressing members 300 may be brought into close contact with the inner wall (ED1) of the ejaculatory duct (ED).

Although the close contact of the pressing members with the inner wall (ED1) of the ejaculatory duct (ED) increases the internal pressure of the ejaculatory duct (ED), the pressing members can prevent the male contraceptive device from moving in the ejaculatory duct (ED).

Although the present invention has been described herein with reference to the foregoing specific embodiments, these embodiments do not serve to limit the invention and are set forth for illustrative purposes. It will be apparent to those skilled in the art that modifications and improvements can be made without departing from the spirit and scope of the invention.

Simple modifications and changes of the present invention belong to the scope of the present invention and the specific scope of the present invention will be clearly defined by the appended claims.

INDUSTRIAL APPLICABILITY

The male contraceptive device of the present invention is easy to insert into and remove from the ejaculatory duct while minimizing side effects and sequelae. In addition, the male contraceptive device of the present invention can be used semi-permanently with good contraceptive efficacy. Therefore, the present invention is considered industrially applicable.

The invention claimed is:

1. A male contraceptive device comprising: a tube having an internal hollow whose both ends are open and insertable into an ejaculatory duct; and at least one filter located in the hollow of the tube, wherein the at least one filter comprises a plurality of microchannels passing therethrough and a plurality of nanospikes formed on a first surface thereof.

2. The male contraceptive device according to claim 1, wherein the male contraceptive device comprises a plurality of pressing members arranged on an outer surface of the tube and spaced apart from each other.

3. The male contraceptive device according to claim 2, wherein the tube further comprises a partition wall located in the hollow to partition the hollow into an inner space and an outer space and a plurality of second through-holes penetrating an inner surface in contact with the outer space and the outer surface, and the outer space is located outside the inner space to surround the inner space.

4. The male contraceptive device according to claim 3, wherein each of the pressing members comprises a second pressing portion having a second accommodation space therein and a second connection portion connecting the second pressing portion and the tube and having a second connection hole through which a corresponding second through-hole is in communication with the second accommodation space.

5. The male contraceptive device according to claim 2, wherein the tube further comprises a plurality of first through-holes penetrating an inner surface thereof in contact with the hollow and the outer surface thereof and each of the pressing members comprises a first pressing portion having a first accommodation space therein and a first connection portion connecting the first pressing portion and the tube and having a first connection hole through which a corresponding first through-hole is in communication with the first accommodation space.

6. The male contraceptive device according to claim 2, wherein the pressing members are arranged at regular intervals along a circumference of the tube.

7. The male contraceptive device according to claim 1, further comprising a movement-preventing member located at one side of the tube and surrounding the tube, wherein the movement-preventing member is made of a material that expands at a preset temperature.

8. The male contraceptive device according to claim 1, wherein the tube is made of a stretchable material.

9. The male contraceptive device according to claim 1, wherein the at least one filter is provided in plurality and the plurality of filters are arranged along a lengthwise direction of the tube.

10. The male contraceptive device according to claim 1, wherein the tube further comprises a flange member protruding from an inner surface to support a second surface of the at least one filter.

* * * * *